(12) United States Patent
Zones et al.

(10) Patent No.: US 10,167,200 B2
(45) Date of Patent: Jan. 1, 2019

(54) SYNTHESIS OF MOLECULAR SIEVE SSZ-41

(71) Applicant: Chevron U.S.A. Inc., San Ramon, CA (US)

(72) Inventors: Stacey Ian Zones, San Francisco, CA (US); Cong-Yan Chen, Kensington, CA (US); Howard Steven Lacheen, Richmond, CA (US); Kaustav Chaudhuri, San Francisco, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 15/729,707

(22) Filed: Oct. 11, 2017

(65) Prior Publication Data

US 2018/0162738 A1 Jun. 14, 2018

Related U.S. Application Data

(60) Provisional application No. 62/433,476, filed on Dec. 13, 2016.

(51) Int. Cl.
*C01B 39/48* (2006.01)
*B01J 29/04* (2006.01)
*B01J 29/74* (2006.01)
*B01J 37/04* (2006.01)
*B01J 37/30* (2006.01)
*C07C 5/27* (2006.01)
*B01J 37/00* (2006.01)
*C01B 39/02* (2006.01)

(52) U.S. Cl.
CPC ............ *C01B 39/48* (2013.01); *B01J 29/048* (2013.01); *B01J 29/74* (2013.01); *B01J 37/0018* (2013.01); *B01J 37/04* (2013.01); *B01J 37/30* (2013.01); *C01B 39/026* (2013.01); *C07C 5/2724* (2013.01); *B01J 2229/183* (2013.01); *C07C 2523/44* (2013.01)

(58) Field of Classification Search
CPC ..... C01B 39/48; B01J 29/048; B01J 29/7049; B01J 29/74
See application file for complete search history.

(56) References Cited

U.S. PATENT DOCUMENTS

| | | |
|---|---|---|
| 5,591,421 A | 1/1997 | Zones |
| 5,656,149 A | 8/1997 | Zones et al. |
| 2011/0318262 A1 | 12/2011 | Zones et al. |
| 2016/0243531 A1 | 8/2016 | Dusselier et al. |
| 2018/0162738 A1* | 6/2018 | Zones .................. C01B 39/026 |

OTHER PUBLICATIONS

PCT International Search Report, International Patent Appl. No. PCT/US2017/056036, dated Jan. 30, 2018.

* cited by examiner

*Primary Examiner* — David M Brunsman
(74) *Attorney, Agent, or Firm* — Terrence Flaherty

(57) ABSTRACT

A method is disclosed for synthesizing zincoaluminosilicate molecular sieve SSZ-41 having high aluminum content from a combined source of silicon oxide and aluminum oxide selected from one or more a FAU framework type zeolite and a colloidal aluminosilicate.

7 Claims, 3 Drawing Sheets

SYNTHESIS OF MOLECULAR SIEVE SSZ-41

CROSS REFERENCE TO RELATED APPLICATIONS

This application claims priority to U.S. Provisional Application Ser. No. 62/433,476, filed on Dec. 13, 2016, the disclosure of which is fully incorporated herein by reference.

TECHNICAL FIELD

The present disclosure relates to the synthesis of zincoaluminosilicate molecular sieve SSZ-41.

BACKGROUND

Molecular sieve materials, both natural and synthetic, have been demonstrated in the past to be useful as adsorbents and to have catalytic properties for various types of hydrocarbon conversion reactions. Certain molecular sieves, such as zeolites, silicoaluminophosphates, aluminophosphates, and mesoporous materials, are ordered, porous crystalline materials having a definite crystalline structure as determined by X-ray diffraction. Within a crystalline molecular sieve material there are cavities which may be interconnected by channels or pores. These cavities and pores are uniform in size within a specific molecular sieve material. Because the dimensions of these pores are such as to accept for adsorption molecules of certain dimensions while rejecting those of larger dimensions, these materials have come to be known as "molecular sieves" and are utilized in a variety of industrial processes.

U.S. Pat. No. 5,591,421 discloses a zinco(alumino)silicate molecular sieve designated SSZ-41 and its synthesis using a polymethylene diquat compound as a structure directing agent, such as α,ω-di(N-methylpiperidine)polymethylene dicationic compounds and α,ω-di(1,4-diazabicyclo[2.2.2]octane)polymethylene dicationic compounds. SSZ-41 appears to be closely related in structure to high-silica molecular sieve VPI-8 (VET framework type) but differs from VPI-8 in that SSZ-41 has an argon adsorption capacity greater than (e.g., up to about three times) that reported for VPI-8.

According to the present disclosure, it has now been found that zincoaluminosilicate SSZ-41 having high aluminum content can be directly synthesized from a combined source of silicon oxide and aluminum oxide selected from one or more of FAU framework type zeolite and a colloidal aluminosilicate.

SUMMARY

In one aspect, there is provided a method of synthesizing a zincoaluminosilicate molecular sieve having the framework structure of SSZ-41, the method comprising: (a) preparing a reaction mixture comprising: (1) a combined source of silicon oxide and aluminum oxide selected from a FAU framework type zeolite, a colloidal aluminosilicate, or a mixture thereof; (2) a source of zinc; (3) a source of a Group 1 or Group 2 metal; (4) a structure directing agent comprising 1,1'-(1,4-butanediyl)bis-4-aza-1-azoniabicyclo[2.2.2]octane dications; (5) hydroxide ions; and (6) water; and (b) subjecting the reaction mixture to crystallization conditions sufficient to form crystals of the molecular sieve.

BRIEF DESCRIPTION OF THE DRAWINGS

FIG. 3 is a plot of n-decane conversion as a function of temperature.

FIG. 4 is a plot of n-decane conversion as a function of temperature.

DETAILED DESCRIPTION

Introduction

Figure 1:
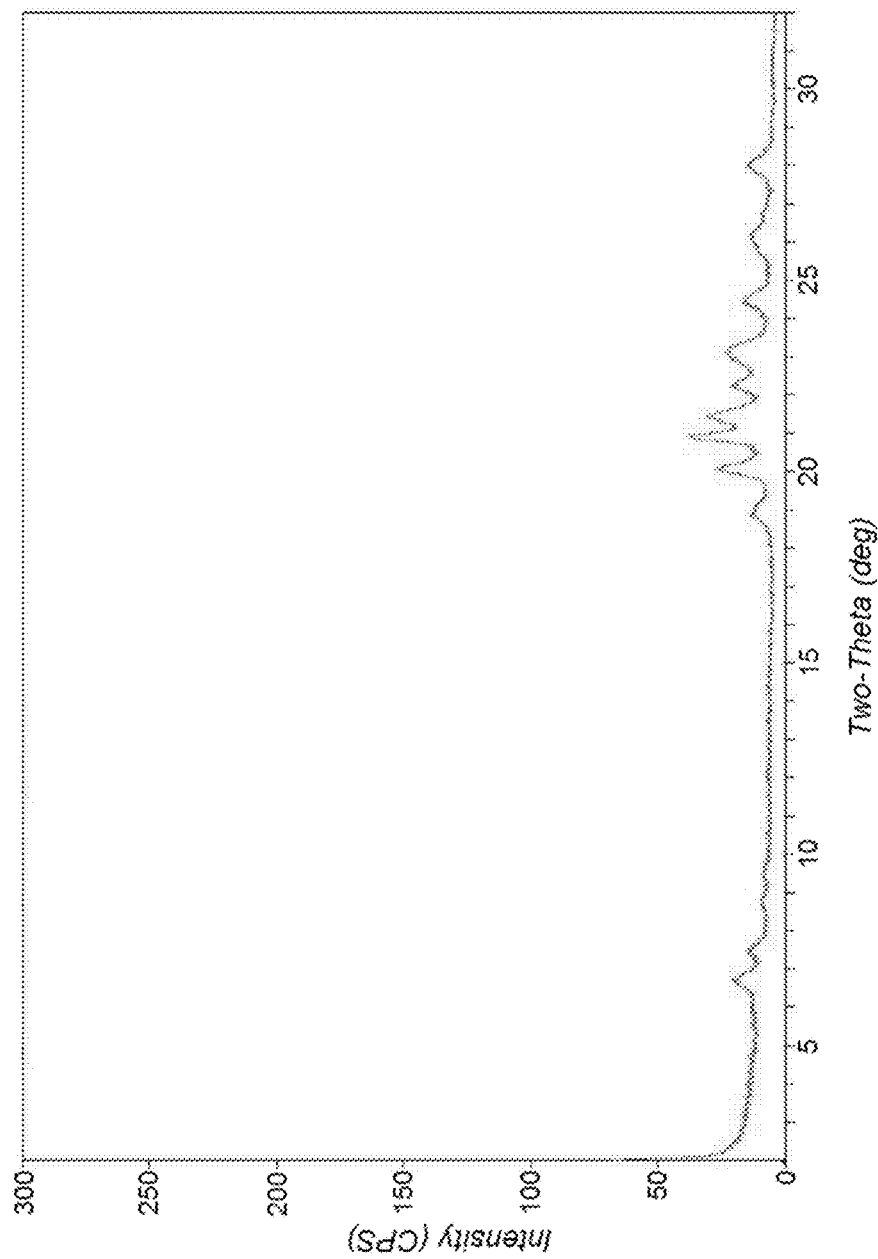
FIG. 1 is a powder X-ray diffraction (XRD) pattern of the as-synthesized molecular sieve prepared in Example 3.

The term "zincoaluminosilicate" refers to a crystalline microporous solid including silicon, aluminum, and zinc oxides within its framework structure. Such zincoaluminosilicates may be "pure-zincoaluminosilicates" (i.e., absent other detectable metal oxides within the framework) or optionally substituted. When described as "optionally substituted," the respective framework may contain boron, gallium, hafnium, iron, tin, titanium, indium, vanadium, zirconium, or other atoms substituted for one or more of the aluminum, silicon, or zinc atoms not already present in the framework structure.

The term "framework type" is used in the sense described in the "*Atlas of Zeolite Framework Types*," Sixth Revised Edition, Elsevier, 2007.

The term "as-synthesized" is employed herein to refer to a molecular sieve in its form after crystallization, prior to removal of the structure directing agent.

The term "anhydrous" is employed herein to refer to a molecular sieve substantially devoid of both physically adsorbed and chemically adsorbed water.

The term "colloid" and other like terms including "colloidal," "sol," and the like refer to a two-phase system having a dispersed phase and a continuous phase. The colloids of the present disclosure have a solid phase dispersed or suspended in a continuous or substantially continuous liquid phase, typically an aqueous solution. Colloids are stable mixtures and the dispersed phase generally does not settle out of the mixture.

As used herein, the numbering scheme for the Periodic Table Groups is as disclosed in *Chem. Eng. News* 1985, 63(5), 26-27.

Reaction Mixture

In general, the present zincoaluminosilicate molecular sieve is synthesized by: (a) preparing a reaction mixture comprising (1) a combined source of silicon oxide and aluminum oxide selected from a FAU framework type zeolite, a colloidal aluminosilicate, or a mixture thereof; (2) a source of zinc; (3) a source of a Group 1 or Group 2 metal (M); (4) a structure directing agent (Q) comprising 1,1'-(1,4-butanediyl)bis-4-aza-1-azoniabicyclo[2.2.2]octane dications; (5) hydroxide ions; and (6) water; and (b) subjecting the reaction mixture to crystallization condition sufficient to form crystals of the molecular sieve.

The composition of the reaction mixture from which the molecular sieve is formed, in terms of molar ratios, is identified in Table 1 below:

TABLE 1

| Reactants | Useful | Exemplary |
| --- | --- | --- |
| $SiO_2/Al_2O_3$ | 50 to 150 | 60 to 90 |
| $SiO_2/ZnO$ | 15 to 75 | 20 to 40 |
| $M/SiO_2$ | 0.05 to 0.35 | 0.10 to 0.30 |
| $Q/SiO_2$ | 0.10 to 0.50 | 0.15 to 0.40 |
| $OH/SiO_2$ | 0.10 to 0.50 | 0.15 to 0.40 |
| $H_2O/SiO_2$ | 10 to 60 | 15 to 45 | wherein M and Q are as described herein above.

The source of silicon oxide and aluminum oxide employed herein is an aluminosilicate source. The source of silicon oxide and aluminum oxide may be selected from a FAU framework type zeolite, a colloidal aluminosilicate, or a mixture thereof.

Suitable FAU framework type zeolites are commercially available from, for example, Zeolyst International (Conshohocken, Pa.) and Tosoh Corporation (Tokyo, Japan). The FAU framework type zeolite may have a $SiO_2/Al_2O_3$ molar ratio in a range of 50 to 100 (e.g., 50 to 95, 50 to 90, 50 to 85, 50 to 80, 55 to 100, 55 to 95, 55 to 90, 55 to 85, 55 to 80, 60 to 100, 60 to 95, 60 to 90, 60 to 85, or 60 to 80).

Suitable colloidal aluminosilicates are described, for example, in U.S. Patent Application Publication No. 2005/0234136.

In some aspects, the reaction mixture may be substantially free of a separate source of intentionally added silicon oxide (e.g., colloidal silica, precipitated silica, fumed silica, alkali metal silicates, and tetraalkyl orthosilicates) and/or a separate source of intentionally added aluminum oxide (e.g., hydrated alumina, alkali metal aluminates, aluminum alkoxides, and water-soluble aluminum salts such as aluminum nitrate).

Suitable sources of zinc include zinc oxide, zinc halides, zinc nitrate, and zinc acetate.

Examples of suitable Group 1 or Group 2 metals (M) include sodium, potassium and calcium, with sodium being preferred. The metal (M) is generally present in the reaction mixture as the hydroxide.

The structure directing agent (Q) comprises a 1,1'-(1,4-butanediyl)bis-4-aza-1-azoniabicyclo[2.2.2]octane dication ("DABCO-$C_4$-DABCO") of the following structure (1):

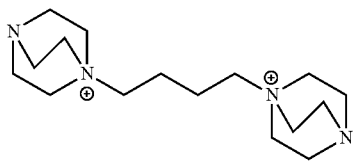

(1)

Suitable sources of Q are the hydroxides, chlorides, bromides, and/or other salts of the diquaternary ammonium compound.

The reaction mixture may contain seeds of a molecular sieve material, such as SSZ-41 from a previous synthesis, desirably in an amount of from 0.01 to 10,000 ppm by weight (e.g., from 100 to 5000 ppm by weight) of the reaction mixture.

For each embodiment described herein, the reaction mixture can be supplied by more than one source. Also, two or more reaction components can be provided by one source.

The reaction mixture can be prepared either batch wise or continuously. Crystal size, morphology and crystallization time of the present molecular sieve can vary with the nature of the reaction mixture and the crystallization conditions.

Crystallization and Post-Synthesis Treatment

Crystallization of the present molecular sieve from the above reaction mixture can be carried out under either static, tumbled or stirred conditions in a suitable reactor vessel, such as for example polypropylene jars or Teflon-lined or stainless steel autoclaves, at a temperature of from 125° C. to 200° C. for a time sufficient for crystallization to occur at the temperature used, e.g., from 50 to 500 hours. Crystallization is usually carried out in a closed system under autogenous pressure.

Once crystals of the molecular sieve have formed, the solid product is recovered from the reaction mixture by standard mechanical separation techniques such as centrifugation or filtration. The recovered crystals are water-washed and then dried to obtain the as-synthesized crystals. The drying step is typically performed at a temperature of less than 200° C.

As a result of the crystallization process, the recovered crystalline molecular sieve product contains within its pore structure at least a portion of the structure directing agent used in the synthesis.

The as-synthesized molecular sieve may be subjected to treatment to remove part or all of the organic structure directing agent used in its synthesis. This is conveniently effected by thermal treatment in which the as-synthesized material is heated at a temperature of at least about 370° C. for at least 1 minute and generally not longer than about 24 hours. The thermal treatment can be performed at a temperature up to about 925° C. While sub-atmospheric pressure can be employed for the thermal treatment, atmospheric pressure is desired for reasons of convenience. Additionally or alternatively, the organic structure directing agent can be removed by treatment with ozone (see, e.g., A. N. Parikh et al., *Micropor. Mesopor. Mater.* 2004, 76, 17-22).

The original Group 1 and/or Group 2 metal cations (e.g., Na+) of the as-synthesized molecular sieve can be replaced in accordance with techniques well known in the art by ion exchange with other cations. Illustrative examples of suitable replacing cations include metal ions, hydrogen ions, hydrogen precursor ions (e.g., ammonium ions), and combinations thereof. Preferred replacing cations are those which tailor the catalytic activity for certain organic compound conversion reactions. These include hydrogen, rare earth metals and metals of Groups 2 to 15 of the Periodic Table of Elements.

Characterization of the Molecular Sieve

In its as-synthesized and anhydrous form, the present molecular sieve has a chemical composition, in terms of molar ratios, as described in Table 2:

TABLE 2

|  | Broad | Exemplary |
| --- | --- | --- |
| $SiO_2/Al_2O_3$ | 50 to <100 | 50 to 80 |
| $SiO_2/ZnO$ | 10 to 25 | 10 to 25 |
| $Q/SiO_2$ | >0 to 0.1 | >0 to 0.1 |
| $M/SiO_2$ | >0 to 0.1 | >0 to 0.1 | wherein Q and M are as described herein above.

In some aspects, the $SiO_2/ZnO$ molar ratio may be in a range of 10 to <20 (e.g., 10 to 19, 10 to 18, 10 to 17, 10 to 16, 10 to 15, 12 to 19, 12 to 18, 12 to 17, or 12 to 16).

It should be noted that the as-synthesized form of the present molecular sieve may have molar ratios different from the molar ratios of reactants of the reaction mixture used to prepare the as-synthesized form. This result may occur due to incomplete incorporation of 100% of the reactants of the reaction mixture into the crystals formed (from the reaction mixture).

The present molecular sieve composition may be substantially free of FAU framework type zeolite. By "substantially free of FAU framework type zeolite" is meant that the present molecular sieve composition contains less than 1% (e.g., less than 0.5% or no measurable amount) of FAU framework type zeolite. The amount of FAU framework type zeolite present can be determined by conventional XRD analysis techniques.

As taught by U.S. Pat. No. 5,591,421, molecular sieve SSZ-41 is characterized by a powder X-ray diffraction pattern which, in the as-synthesized form of the molecular sieve, includes at least the peaks listed in Table 3 below and which, in the calcined form of the molecular sieve, includes at least the peaks listed in Table 4 below.

TABLE 3

Characteristic XRD Peaks for As-Synthesized SSZ-41

| 2-Theta[a] | d-Spacing, nm | Relative Intensity[b] |
|---|---|---|
| 6.71 | 1.316 | S |
| 9.52 | 0.928 | W |
| 20.00 | 0.444 | VS |
| 21.40 | 0.415 | VS |
| 22.19 | 0.400 | S-VS |
| 23.22 | 0.383 | S |
| 24.45 | 0.364 | S-VS |
| 26.07 | 0.342 | M-S |
| 28.01 | 0.318 | M |
| 35.52 | 0.253 | M |

[a]±0.10
[b]The powder XRD patterns provided are based on a relative intensity scale in which the strongest line in the X-ray diffraction pattern is assigned a value of 100: W = weak (>0 to ≤20); M = medium (>20 to ≤40); S = strong (>40 to ≤60); VS = very strong (>60 to ≤100).

TABLE 4

Characteristic XRD Peaks for Calcined SSZ-41

| 2-Theta[a] | d-Spacing, nm | Relative Intensity[b] |
|---|---|---|
| 6.82 | 1.295 | VS |
| 9.64 | 0.917 | M-S |
| 20.14 | 0.441 | VS |
| 21.55 | 0.412 | S |
| 22.35 | 0.397 | M |
| 23.38 | 0.380 | M |
| 24.64 | 0.361 | M |
| 26.24 | 0.339 | M |
| 28.18 | 0.316 | M |
| 35.70 | 0.251 | W |

[a]±0.10
[b]The powder XRD patterns provided are based on a relative intensity scale in which the strongest line in the X-ray diffraction pattern is assigned a value of 100: W = weak (>0 to ≤20); M = medium (>20 to ≤40); S = strong (>40 to ≤60); VS = very strong (>60 to ≤100).

The powder X-ray diffraction patterns presented herein were collected by standard techniques. The radiation was CuK$_\alpha$ radiation. The peak heights and the positions, as a function of 2θ where θ is the Bragg angle, were read from the relative intensities of the peaks (adjusting for background), and d, the interplanar spacing corresponding to the recorded lines, can be calculated.

Minor variations in the diffraction pattern can result from variations in the mole ratios of the framework species of the particular sample due to changes in the lattice constants. In addition, sufficiently small crystals will affect the shape and intensity of peaks, leading to significant peak broadening. Minor variations can also result from variations in the organic compound used in the preparation. Notwithstanding these minor perturbations, the basic crystal lattice remains unchanged.

Adsorption and Catalysis

The present molecular sieve can be used as an adsorbent and/or as a catalyst to catalyze a wide variety of organic compound conversion processes including many of present commercial/industrial importance. Examples of chemical conversion processes effectively catalyzed by the present molecular sieve, by itself or in combination with one or more other catalytically active substances including other crystalline catalysts, include those requiring a catalyst with acid activity. Examples of organic compound conversion processes which may be catalyzed by the present molecular sieve include alkylation, cracking, hydrocracking, disproportionation, oligomerization, and isomerization.

The present molecular sieve can be formulated into a catalyst composition by combination with other materials, such as binders and/or matrix materials, which provide additional hardness or catalytic activity to the finished catalyst.

Materials which can be blended with the present molecular sieve can be various inert or catalytically active materials. These materials include compositions such as kaolin and other clays, various forms of rare earth metals, other non-zeolite catalyst components, zeolite catalyst components, alumina or alumina sol, titania, zirconia, quartz, silica or silica sol, and mixtures thereof. These components are also effective in reducing overall catalyst cost, acting as a thermal sink to assist in heat shielding the catalyst during regeneration, densifying the catalyst and increasing catalyst strength. When blended with such components, the amount of SSZ-41 contained in the final catalyst product can range from 1 to 90 wt. % (e.g., 2 to 80 wt. %) of the total catalyst.

EXAMPLES

The following illustrative examples are intended to be non-limiting.

Example 1

SSZ-41 was synthesized according to U.S. Pat. No. 5,591,421. A solution was prepared by dissolving 11.01 g of zinc acetate dihydrate into 450 mL of deionized water. Then, 3 g of FAU framework type zeolite Y-52 ($SiO_2/Al_2O_3$ molar ratio=5) was slurried into the solution. The slurry was allowed to equilibrate at room temperature over several days. The product was collected by filtration, washed several times with deionized water and dried. Analysis of the dried powder showed about 80% exchange of sodium cations (from the Y-52 zeolite) for zinc cations.

4.41 g of a 0.77M solution of DABCO-$C_4$-DABCO dihydroxide was mixed with 2.31 g of 1N NaOH and 2.64 mL of deionized water in a Teflon cup of a 23 mL Parr reactor. Then, 0.28 g of the zinc-exchanged FAU framework type zeolite and 0.72 g of CAB-O-SIL® M-5 fumed silica (Cabot Corporation) were added and the resulting reaction mixture was heated for two weeks at 160° C. with rotation (43 rpm). The mixed phase product was analyzed by powder XRD and showed a diminished quantity of FAU framework type zeolite plus new XRD lines. The product contained several wt. % organic with C/N ratios consistent with the organic structure directing agent.

The reaction was repeated and once again a mixture of phases was produced. The as-synthesized product was slurried in 20 mL of 2N HCl and heated for three days at 85° C. Acid treatment dissolved away unreacted zinc-exchanged FAU framework type zeolite leaving the organo-zeolite phase behind. The product had the powder XRD pattern of SSZ-41.

An additional acid treatment step was required to dissolve the unreacted FAU framework type zeolite and recover the as-synthesized SSZ-41 product. Acid treatment also results in removal of some amount of aluminum intended to be incorporated into SSZ-41.

Example 2

SSZ-41 was synthesized according to U.S. Pat. No. 5,591,421. Two mmoles of DABCO-$C_4$-DABCO dihydroxide was mixed with 2 mmoles of NaOH in 12 mL of deionized water. Next, 0.12 g of zinc acetate dihydrate was added and then 0.90 g of high-silica FAU framework type zeolite HUA-390 (Tosoh, $SiO_2/Al_2O_3$ molar ratio=500). The reaction mixture was placed in a Parr reactor and heated for 6 days at 160° C. with rotation (45 rpm). The settled crystalline was product was collected by filtration, washed with deionized water and dried. The product had the powder XRD pattern of SSZ-41. The product had a $SiO_2/Al_2O_3$ molar ratio of about 200.

Example 3

1.5 mmoles of DABCO-$C_4$-DABCO dihydroxide was mixed with 1.5 mmol of a 1N NaOH solution in a Teflon liner. Deionized water was added to bring the total volume of the mixture to 12 mL. Then, 0.09 g of zinc acetate dihydrate and 0.70 g of FAU framework type zeolite CBV780 (Zeolyst International, $SiO_2/Al_2O_3$ molar ratio=80) were added to the mixture followed by 0.03 g of SSZ-41 seed material. The liner was capped and placed within a Parr steel autoclave reactor. The autoclave was placed in an oven and heated for 8-10 days at 160° C. with rotation (43 rpm). The solid products were recovered from the cooled reactor by filtration, washed with deionized water and dried at 95° C.

Figure 2:
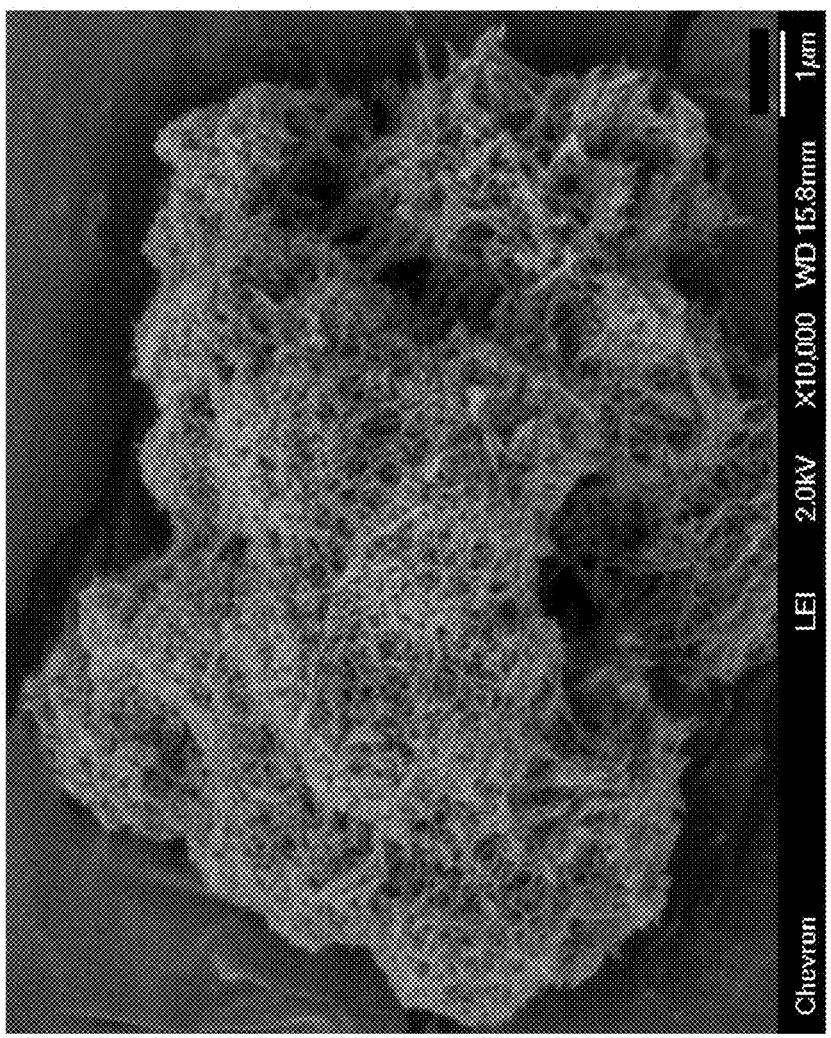
FIG. 2 is a scanning electron micrograph (SEM) image of the as-synthesized molecular sieve prepared in Example 3.

The resulting as-synthesized product was analyzed by powder XRD and shown to be SSZ-41 with no measurable amount of FAU framework type zeolite reactant. The powder XRD pattern is shown in FIG. 1. FIG. 2 is a SEM image of the as-synthesized product and shows a uniform field of very small needle-like crystals.

Two separate product samples were tested by Energy Dispersive X-ray (EDX) analysis for incorporation of aluminum and zinc into the crystals. The results are set forth in Table 5 below.

TABLE 5

|  | Sample 1 | Sample 2 |
|---|---|---|
| Zn, wt. % | 3.85 | 3.11 |
| Al, wt. % | 1.15 | 1.23 |
| Si, wt. % | 43.0 | 43.0 |

The EDX measurements confirmed that aluminum is present in the product.

The as-synthesized product was calcined inside a muffle furnace under a flow of air heated to 595° C. at a rate of 1° C./minute and held at 595° C. for five hours and cooled to ambient temperature.

The calcined material was then treated with 10 mL (per g of molecular sieve) of a 1N ammonium nitrate solution for 2 hours at 90° C. The solution was cooled, decanted off and the same process repeated.

The product ($NH_4$-SSZ-41) after drying was subjected to a micropore volume analysis using $N_2$ as adsorbate and via the B.E.T. method. The molecular sieve exhibited a micropore volume of 0.1096 $cm^3$/g.

Brønsted acidity of the calcined molecular sieve was determined by isopropylamine-temperature-programmed desorption (IPam TPD) adapted from the published descriptions by T. J. Gricus Kofke et al. (*J. Catal.* 1988, 114, 34-45); T. J. Gricus Kofke et al. (*J. Catal.* 1989, 115, 265-272); and J. G. Tittensor et al. (*J. Catal.* 1992, 138, 714-720). A sample was pre-treated at 400° C.-500° C. for 1 hour in flowing dry $H_2$. The dehydrated sample was then cooled down to 120° C. in flowing dry helium and held at 120° C. for 30 minutes in a flowing helium saturated with isopropylamine for adsorption. The isopropylamine-saturated sample was then heated up to 500° C. at a rate of 10° C./minute in flowing dry helium. The Brønsted acidity was calculated based on the weight loss vs. temperature by thermogravimetric analysis (TGA) and effluent $NH_3$ and propene by mass spectrometry. The sample had a Brønsted acidity of 167 μmol/g. This indicates that the aluminum is in the framework of the molecular sieve.

Example 4

A Teflon liner was charged with 2 mmoles of DABCO-$C_4$-DABCO dihydroxide and 2 mmoles of a 1N NaOH solution. Then, 5.4 g of deionized water was added along with 0.12 g of zinc acetate dihydrate. Lastly, 3 g of a sol of aluminum coated onto silica particles (30% solids, $SiO_2/Al_2O_3$ molar ratio=130) was added. The liner was capped and placed within a Parr steel autoclave reactor. The autoclave was placed in an oven and heated for 8 days at 160° C. with rotation (43 rpm). The solid products were recovered from the cooled reactor by filtration, washed with deionized water and dried at 95° C.

Powder XRD indicated that the product was SSZ-41.

The product had an Al enrichment more than double that of conventional SSZ-41.

Example 5

Material from Example 2 was calcined in air at 595° C. for 5 hours. The calcined material was then treated with 10 mL (per g of molecular sieve) of a 1N ammonium nitrate solution at 95° C. for 2 hours. The mixture was cooled, the solvent decanted off and the same process repeated. After drying, the material was loaded with palladium by mixing for three days at room temperature 4.5 g of a 0.148 N $NH_4OH$ solution with 5.5 g of deionized water and then a $(NH_3)_4Pd(NO_3)_2$ solution (buffered at pH 9.5) such that 1 g of this solution mixed in with 1 g of molecular sieve provided a 0.5 wt. % Pd loading. The recovered Pd-exchanged molecular sieve was washed with deionized water, dried at 95° C., and then calcined to 482° C. for 3 hours. The calcined Pd/SSZ-41 catalyst was then pelletized, crushed, and sieved to 20-40 mesh.

Hydroconversion of n-Decane

Figure 3:
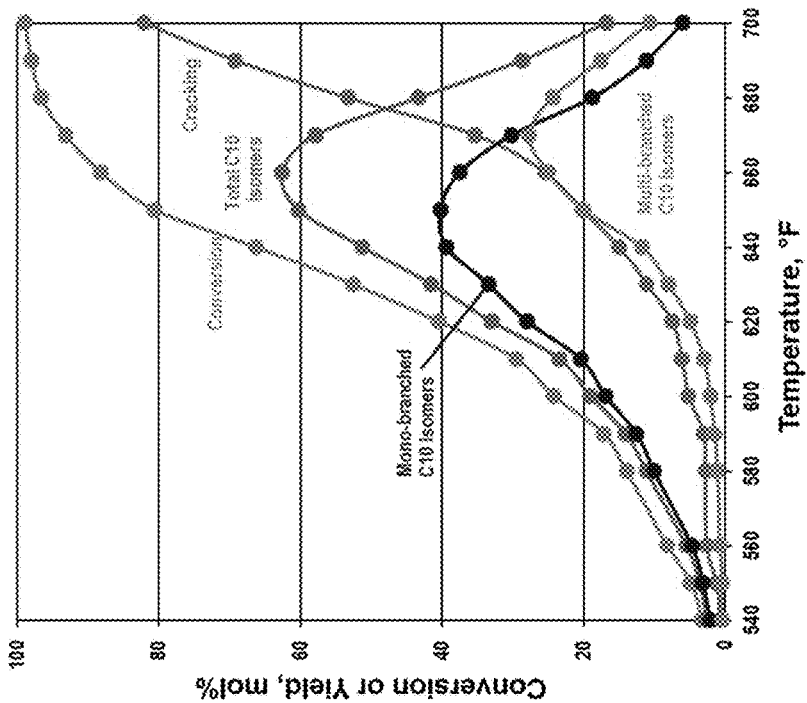
FIG. 3 shows the results of selective hydroconversion of n-decane over the Pd/SSZ-41 catalyst of Example 5. Specifically.

For catalytic testing, 0.5 g of this Pd/SSZ-41 catalyst was loaded in the center of a 23 inch-long by 0.25 inch outside diameter stainless steel reactor tube with alundum loaded upstream of the catalyst for preheating the feed (a total pressure of 1200 psig; a down-flow hydrogen rate of 160 mL/min, when measured at 1 atmosphere pressure and 25° C.; and a down-flow liquid feed rate of 1 mL/hour). All materials were first reduced in flowing hydrogen at about 315° C. for 1 hour. Products were analyzed by on-line capillary gas chromatography (GC) once every thirty minutes. Raw data from the GC was collected by an automated data collection/processing system and hydrocarbon conversions were calculated from the raw data. Conversion is defined as the amount n-decane reacted to produce other products (including iso-$C_{10}$). Yields are expressed as weight percent of products other than n-decane and include iso-$C_{10}$ isomers as a yield product. The results are shown in FIG. 3.

Example 6

Figure 4:
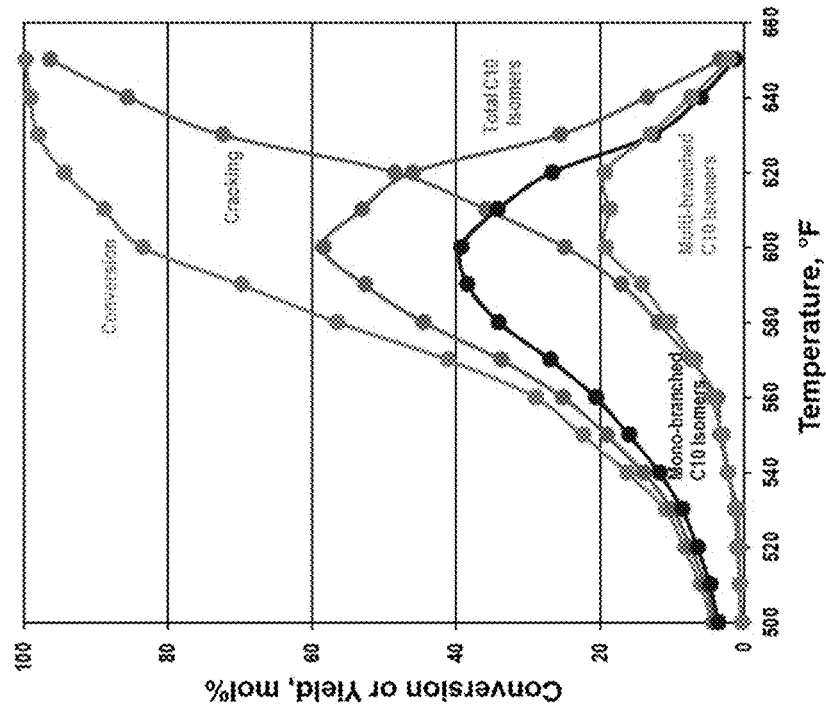
FIG. 4 shows the results of selective hydroconversion of n-decane over the Pd/SSZ-41 catalyst of Example 6. Specifically.

Palladium ion-exchange was carried out on the material from Example 4 per the teachings of Example 5. The palladium-exchanged sample was tested for the selective hydroconversion of n-decane under the conditions described in Example 4. The results are presented in FIG. 4.

The results show that the temperature of reaching maximum isomerization is lower for the catalyst of Example 6 than for the catalyst of Example 5. This is believed to be due to the higher incorporation of aluminum in the catalyst of Example 6.

The invention claimed is:

1. A method of synthesizing a zincoaluminosilicate molecular sieve having the framework structure of SSZ-41, the method comprising:
   (a) preparing a reaction mixture comprising:
      (1) a combined source of silicon oxide and aluminum oxide selected from a FAU framework type zeolite, a colloidal aluminosilicate, or a mixture thereof;
      (2) a source of zinc;
      (3) a source of a Group 1 or Group 2 metal (M);
      (4) a structure directing agent (Q) comprising 1,1'-(1,4-butanediyl)bis-4-aza-1-azoniabicyclo[2.2.2]octane dications;
      (5) hydroxide ions; and
      (6) water; and
   (b) subjecting the reaction mixture to crystallization conditions sufficient to form crystals of the molecular sieve;
   wherein the reaction mixture has a composition, in terms of molar ratios, as follows:

| | |
|---|---|
| $SiO_2/Al_2O_3$ | 60 to 90 |
| $SiO_2/ZnO$ | 15 to 40 |
| $M/SiO_2$ | 0.10 to 0.30 |
| $Q/SiO_2$ | 0.15 to 0.40 |
| $OH/SiO_2$ | 0.15 to 0.40 |
| $H_2O/SiO_2$ | 15 to 45. |

2. The method of claim 1, wherein the reaction mixture is substantially free of a separate source of intentionally added silicon oxide.

3. The method of claim 1, wherein the reaction mixture is substantially free of a separate source of intentionally added aluminum oxide.

4. The method of claim 1, wherein the reaction mixture further comprises seeds.

5. The method of claim 4, wherein the reaction mixture comprises from 0.01 ppm by weight to 10,000 ppm by weight of seeds.

6. The method of claim 4, wherein the seeds comprise a molecular sieve material having the framework structure of SSZ-41.

7. The method of claim 1, wherein the crystallization conditions include a temperature of from 125° C. to 200° C.

* * * * *